United States Patent
Aihara et al.

(10) Patent No.: US 11,328,792 B2
(45) Date of Patent: May 10, 2022

(54) DEVICE FOR DETECTING A DYNAMICAL NETWORK BIOMARKER, METHOD FOR DETECTING SAME, AND PROGRAM FOR DETECTING SAME

(71) Applicant: Japan Science and Technology Agency, Kawaguchi (JP)

(72) Inventors: Kazuyuki Aihara, Tokyo (JP); Luonan Chen, Kobe (JP); Rui Liu, Guangzhou (CN); Zhiping Liu, Jinan (CN); Meiyi Li, Shanghai (CN)

(73) Assignee: Japan Science and Technology Agency, Kawaguchi (JP)

( * ) Notice: Subject to any disclaimer, the term of this patent is extended or adjusted under 35 U.S.C. 154(b) by 331 days.

(21) Appl. No.: 14/430,724

(22) PCT Filed: Feb. 12, 2013

(86) PCT No.: PCT/JP2013/053188
§ 371 (c)(1),
(2) Date: Mar. 24, 2015

(87) PCT Pub. No.: WO2014/050160
PCT Pub. Date: Apr. 3, 2014

(65) Prior Publication Data
US 2015/0278433 A1     Oct. 1, 2015

(30) Foreign Application Priority Data
Sep. 26, 2012  (JP) .............................. JP2012-211921

(51) Int. Cl.
*G01N 33/48*   (2006.01)
*G01N 33/50*   (2006.01)
(Continued)

(52) U.S. Cl.
CPC ............. *G16B 20/20* (2019.02); *G16B 20/00* (2019.02); *G16B 30/00* (2019.02); *G16B 40/00* (2019.02); *G16B 20/10* (2019.02)

(58) Field of Classification Search
CPC ........ G16B 20/20; G16B 20/00; G16B 30/00; G16B 40/00; G16B 20/10
See application file for complete search history.

(56) References Cited

U.S. PATENT DOCUMENTS

| | | | |
|---|---|---|---|
| 2004/0014059 A1 | 1/2004 | Liew | |
| 2004/0037841 A1 | 2/2004 | Liew | |

(Continued)

FOREIGN PATENT DOCUMENTS

| | | |
|---|---|---|
| JP | 2007528704 A | 10/2007 |
| WO | 2004/112589 A2 | 12/2004 |

OTHER PUBLICATIONS

Hirata et al. Reconstructing state spaces from multivariate data using variable delays. Physical Review E, 2006, article 026202, pp. 1-6.*

(Continued)

*Primary Examiner* — Russell S Negin
(74) *Attorney, Agent, or Firm* — Locke Lord LLP

(57) ABSTRACT

The present invention provides a device, method, and program for detection of a biomarker candidate that may be used in a diagnosis of a pre-disease state indicating a transition from a healthy state to a disease state. Biological samples are collected from a subject to be measured at different times. Statistical data is obtained by aggregating measurement data obtained in measurement on collected biological samples. Thereafter, a process of obtaining high-throughput data (s1), a process of choosing differential biological molecules (s2), a process of clustering (s3), a process of choosing a DNB candidate (s4), and a process of (Continued)

identifying a DNB by significance analysis (s5) are carried out.

9 Claims, 15 Drawing Sheets

(51) Int. Cl.
    *G16B 20/20* (2019.01)
    *G16B 20/00* (2019.01)
    *G16B 30/00* (2019.01)
    *G16B 40/00* (2019.01)
    *G16B 20/10* (2019.01)

(56) References Cited

U.S. PATENT DOCUMENTS

| | | |
|---|---|---|
| 2004/0241729 A1 | 12/2004 | Liew |
| 2005/0123938 A1 | 6/2005 | Liew |
| 2005/0196764 A1 | 9/2005 | Liew |
| 2006/0078574 A1* | 4/2006 | Lichtenberger ........ A61K 9/127 424/400 |
| 2006/0134635 A1 | 6/2006 | Liew |
| 2007/0031841 A1 | 2/2007 | Liew |
| 2007/0054282 A1 | 3/2007 | Liew |
| 2011/0065602 A1 | 3/2011 | Liew |
| 2012/0165212 A1 | 6/2012 | Liew |
| 2013/0102484 A1 | 4/2013 | Liew |
| 2013/0324434 A1 | 12/2013 | Liew |

OTHER PUBLICATIONS

Honda et al. Differential gene expression between chronic hepatitis B and C hepatic lesion. Gastroenterology, 2001, vol. 120, pp. 955-966.*

Van Nes et al. Slow recovery from perturbations as a generic indicator of a nearby catastrophic shift. The American Naturalist, vol. 169, 2007, pp. 738-747.*

Van der Rest et al. Functions of the membrane-associated and cytoplasmic malate dehydrogenases in the citric acid cycle of *Escherichia coli.* Journal of Bacteriology, pp. 6892-6899. (Year: 2000).*

J. G. Venegas et al., "Self-organized patchiness in asthma as a prelude to catastrophic shifts," Nature vol. 434, Apr. 7, 2005, pp. 777-782.

P.E. McSharry et al., "Prediction of epileptic seizures: are nonlinear methods relevant?," Nature Medicine, vol. 9, No. 3, Mar. 2003, pp. 241-245.

R. Pastor-Barriuso et al., "Transition models for change-point estimation in logistic regression," Statistics in Medicine, vol. 22, 2003, pp. 1141-1162.

S. H. Paek et al., "Hearing preservation after gamma knife stereotactic radiosurgery of vestibular schwannoma," Cancer, vol. 104, No. 3, Aug. 1, 2005, pp. 580-590.

J. K. Liu et al., "Pituitary Apoplexy," Seminars in Neurosurgery, vol. 12, No. 3, 2001, pp. 315-320.

G. Tanaka et al., "Bifurcation analysis on a hybrid systems model of intermittent hormonal therapy for prostate cancer," Physics D 237, 2008, pp. 2616-2627.

L. Chen et al., "Detecting early-warning signals for sudden deterioration of complex diseases by dynamical network biomarkers," Scientific Reports, 2: 342, Mar. 29, 2012, pp. 1-8.

T. Shiraishi, et al., "Large-Scale Analysis of Network Bistability for Human Cancers," PLoS Computational Biology, vol. 6, Issue 7, Jul. 2010, e1000851, pp. 1-12. (cited in the Aug. 20, 2019 Office Action issued for KR10-2015-7010816).

E. Ruiz-Garcia, et al., "Gene expression profiling identified Fibronectin I and CXCL9 as candidate biomarkers for breast cancer screening," British Journal of Cancer, 102(3), 2010, pp. 462-468. (cited in the Aug. 20, 2019 Office Action issued for KR10-2015-7010816).

* cited by examiner

| Subjects to be diagnosed | Mice (CD-1 male mice) with carbon oxychloride-induced lung disorder |
|---|---|
| Source of samples | Lung tissues of mice of case group (subject)<br>Lung tissues of mice of control group (referent) |
| Sampling points | 0, 0.5, 1, 4, 8, 12, 24, 48, 72 (h) |
| Targets to be observed | 22,690 genes |

Figure.16

| Source of samples | B-cell lymphoma patient | | | |
|---|---|---|---|---|
| Sampling period | Pathological changes | No. of samples | Splenomegaly | Flow Cytometry |
| P1 | Rest period | 5 | None | Normal rest |
| P2 | Active period | 3 | None | Normal active |
| P3 | Limit period | 6 | +/- | Abnormal |
| P4 | Metastasis period | 5 | + | Mixed |
| P5 | Invasion period | 7 | +++ | B-1 clone |
| Case group | Samples collected in P2 to P5 | | | |
| Control group | Samples collected in P1 | | | |
| Targets to be observed | 13,712 genes | | | |

Figure.17A

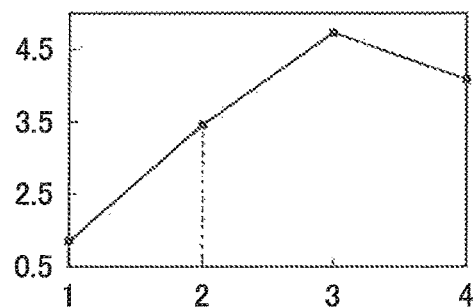

DEVICE FOR DETECTING A DYNAMICAL NETWORK BIOMARKER, METHOD FOR DETECTING SAME, AND PROGRAM FOR DETECTING SAME

TECHNICAL FIELD

The present invention relates to devices, methods, and programs for detecting a biomarker candidate that could be an index for a symptom of a biological object based on measurement data on a plurality of factors obtained by measurement on the biological object.

BACKGROUND ART

It has been identified that a sudden change of a system state exists widely in ecosystems, climate systems, economics and global finance. Such a change often occurs at a critical threshold, or the so-called "tipping point", at which the system shifts abruptly from one state to another. Evidence has been found suggesting that the similar phenomena exist in clinical medicine, that is, during the progression of many complex diseases, e.g., in chronical diseases such as cancer, the deterioration is not necessarily smooth but abrupt (see, for example, non-patent documents 1 to 5). In other words, there exists a sudden catastrophic shift during the process of gradual health deterioration that results in a drastic transition from a healthy state to a disease state. In order to describe the underlying dynamical mechanism of complex diseases, their evolutions are often modeled as time-dependent nonlinear dynamical systems, in which the abrupt deterioration is viewed as the phase transition at a bifurcation point, e.g., for cancer and, asthma attacks.

FIG. 1 is a schematic illustration of the dynamical features of disease progression from a normal state to a disease state through a pre-disease state. Portions (b), (c), and (d) of FIG. 1 are graphs of a potential function representing the stability of the aforementioned modeled system during the progression process by means of the location of black dots with the elapsed time on the horizontal axis and the values of the potential function on the vertical axis.

(a) Deterioration progress of disease.

(b) The normal state is a steady state or a minimum of a potential function, representing a relatively healthy stage.

(c) The pre-disease state is situated immediately before the tipping point and is the limit of the normal state but with a lower recovery rate from small perturbations. At this stage, the system is sensitive to external stimuli and still reversible to the normal state when appropriately interfered with, but a small change in the parameters of the system may suffice to drive the system into collapse, which often implies a large phase transition to the disease state.

(d) The disease state is the other stable state or a minimum of the potential function, where the disease has seriously deteriorated and thus the system is usually irreversible to the normal state.

(e)-(g) The three states are schematically represented by a molecular network where the correlations and deviations of different species are described by the thickness of edges and the colors of nodes respectively.

Therefore, if the pre-disease state is detected, and the patient is notified of the progression process being in a transition to the disease state before the disease state actually arrives, it is likely that the patient can recover from the pre-disease state to the normal state if appropriately treated.

In other words, if the tipping point (critical threshold) is detected, a critical transition can be predicted, which enables an early diagnosis of a disease.

Biomarkers have been conventionally used for the diagnosis of disease state. Typical traditional biomarkers include body fluids, such as serum and urine, that are collected from a biological object; and molecular-level DNA, RNA, protein, metabolites, etc. that are contained in tissues and can be indices through which one can quantitatively know biological changes in a biological object. A disease has been conventionally diagnosed using a biomarker by comparing a biomarker extracted from a normal sample (collected in a healthy state) and a biomarker extracted from an abnormal sample (collected in a disease state).

CITATION LIST

Non-Patent Literature

Non-patent Document 1: "Self-organized patchiness in asthma as a prelude to catastrophic shifts" (U.K.), by Venegas, J. G., et al., Nature, Nature Publishing Group, 2005, Vol. 434, pp. 777-782.

Non-patent Document 2: "Prediction of epileptic seizures: are nonlinear methods relevant?" (U.K.), by McSharry, P. E., Smith, L. A., and Tarassenko, L, Nature Medicine, Nature Publishing Group, 2003, Vol. 9, pp. 241-242.

Non-patent Document 3: "Transition models for change-point estimation in logistic regression" (U.S.A.), by Roberto, P. B., Eliseo, G., and Josef, C., Statistics in Medicine, Wiley-Blackwell, 2003, Vol. 22, pp. 1141-1162.

Non-patent Document 4: "Hearing preservation after gamma knife stereotactic radiosurgery of vestibular schwannoma" (U.S.A.), by Paek, S., et al., Cancer, Wiley-Blackwell, 2005, Vol. 1040, pp. 580-590.

Non-patent Document 5: "Pituitary Apoplexy" (U.S.A.), by Liu, J. K., Rovit, R. L., and Couldwell, W. T., Seminars in neurosurgery, Thieme, 2001, Vol. 12, pp. 315-320.

Non-patent Document 6: "Bifurcation analysis on a hybrid systems model of intermittent hormonal therapy for prostate cancer" (U.S.A.), by Tanaka, G., Tsumoto, K., Tsuji, S., and Aihara, K., Physical Review, American Physical Society, 2008, Vol. 237, pp. 2616-2627.

SUMMARY OF THE INVENTION

Problems to be Solved by the Invention

However, in the case of complex diseases, it is notably hard to predict such critical transitions for the following reasons.

First, because a pre-disease state is a limit of the normal state, the state of the system may show little apparent change before the tipping point is reached. Thus, the diagnosis by traditional biomarkers and snapshot static measurements may not be effective to distinguish those two states (FIGS. 1*b, c*).

Second, despite considerable research efforts, no reliable disease model has been developed to accurately detect the early-warning signals. In particular, deterioration processes may be considerably different even for the same subtype of a disease, depending on individual variations, which makes model-based prediction methods fail for many cases.

Third and most importantly, detecting the pre-disease state must be an individual-based prediction, however, usually there are only a few of samples available for each individual, unlike many other complex systems that are measured over a long term with a large number of samples.

Besides, the conventional diagnosis of diseases by traditional biomarkers involves a comparison of the normal state and the disease state. The patient is already in the disease state at the time of diagnosis, and it is difficult to reverse the disease process to the preceding normal state.

In contrast, the present invention has an object of providing a device, method, and program capable of detecting a pre-disease state which precedes a transition to a disease state and also of providing, for example, a detection device that does not require a disease model and that is capable of assisting diagnosis based only on a small number of biological samples.

Solution to Problem

A device in accordance with the present invention, to achieve the object, is a device for detecting a candidate for a biomarker based on measurement data on a plurality of factors obtained in measurement on a biological object to be measured, the biomarker being an index of a symptom of the biological object, the device including: classification means for classifying factors into clusters based on a correlation of time-dependent changes of measurement data for each factor; choosing means for choosing one of the clusters that satisfies choice conditions that are predetermined based on a correlation of time-dependent changes of measurement data for each factor and time-dependent changes of measurement data among different factors; and detection means for detecting a factor in the chosen cluster as a candidate for a biomarker.

A detection device with these features is capable of detecting a biomarker candidate that serves as an early-warning signal indicating a pre-disease state that precedes a transition from a normal state to a disease state. If a biomarker is identified, the pre-disease state is detected by collecting only a small number of samples from the object to be detected.

The device in accordance with the present invention is such that the choosing means includes: means for calculating, as a first index, an average of values representing a correlation of measurement data for each factor in a cluster; means for calculating, as a second index, an average of values representing a correlation of measurement data on a factor inside the cluster with measurement data on a factor outside the cluster; and means for calculating, as a third index, an average standard deviation of measurement data for each factor in a cluster, the device choosing one of the clusters that contains a factor to be a biomarker based on the first, second, and third indices.

Therefore, the features of each cluster can be quantitatively evaluated using the first index, the second index, and the third index. That enables easy choice of a biomarker.

The device in accordance with the present invention is such that the choosing means chooses one of the clusters that has a maximum composite index based on a product of the first index, the second index, and a reciprocal of the third index.

Therefore, choice of a cluster based on the composite index increases the reliability of the factor that is a biomarker candidate.

The device in accordance with the present invention further includes difference verification means for verifying whether or not the measurement data for each factor has significantly changed with time, wherein the classification means classifies factors that are verified to have changed significantly with time.

Therefore, choice of a factor that has chronologically noticeably changed enables efficient detection of a biomarker candidate from huge measurement data.

The device in accordance with the present invention is such that the difference verification means verifies, based on a comparison of the measurement data for each factor and reference data that is predetermined for each factor and each time series, whether or not the measurement data for each factor has significantly changed with time.

Therefore, obtaining, as reference data, a biological sample that serves as a reference in addition to the measurement data on a plurality of factors that are objects to be detected enables comparison of the measurement data and the reference data and detection free from external disturbance.

The device in accordance with the present invention further includes: means for calculating, for each factor, a reference standard deviation representing an average standard deviation of corresponding reference data and a reference correlation value representing an average of values representing a correlation among different factors, wherein the detection means detects an item in one of the clusters as a candidate for a biomarker if the first index has increased significantly over the reference standard deviation, the second index has decreased significantly over the reference correlation value, and the third index has increased significantly over the reference standard deviation.

Therefore, it may be determined whether or not the chosen factor can be a suitable biomarker.

The device in accordance with the present invention is such that the detection means includes means for verifying significance of a plurality of factors in a cluster based on a statistical value of measurement data and if the significance is verified, detects an item in that cluster as a candidate for a biomarker.

The verification minimizes detection error.

The device in accordance with the present invention is such that the plurality of factors include a gene-related measured item, a protein-related measured item, a metabolite-related measured item, or a measured item related to an image obtained from the biological object.

Therefore, by using a gene-, protein-, or metabolite-related measured item as a factor, biological changes in a biological object can be quantitatively known, and the reliability of detection results can be improved.

A method in accordance with the present invention is a detection method using a device for detecting a candidate for a biomarker based on measurement data on a plurality of factors obtained in measurement on a biological object to be measured, the biomarker being an index of a symptom of the biological object, the device implementing: the classification step of classifying factors into clusters based on a correlation of time-dependent changes of measurement data for each factor; the choosing step of choosing one of the clusters that satisfies choice conditions that are predetermined based on a correlation of time-dependent changes of measurement data for each factor and time-dependent changes of measurement data among different factors; and the detection step of detecting a factor in the chosen cluster as a candidate for a biomarker.

Another method in accordance with the present invention is a method for detecting a candidate for a biomarker based on measurement data on a plurality of factors obtained in measurement on a biological object to be measured, the biomarker being an index of a symptom of the biological object, the method including: the molecular screening step of calculating differential biological molecules from high-throughput data obtained from individual biological samples collected at different times; the clustering step of classifying the differential biological molecules chosen in the molecular screening step into clusters so that closely correlated biological molecules are in a single cluster; the candidate choosing step of prefetching, as the candidate of a biomarker, one of the clusters obtained in the clustering step in which there are a maximum increase in a correlation among biological molecules, a maximum increase in a standard deviation of biological molecules, and a maximum decrease in a correlation of a biological molecule with another biological molecule; and the determination step of determining by a significance test whether or not the candidate for a biomarker chosen in the candidate choosing step is the biomarker.

Detection methods with these features are capable of detecting a biomarker candidate that serves as an early-warning signal indicating a pre-disease state that precedes a transition from a normal state to a disease state. If a biomarker is identified, the pre-disease state is detected by collecting only a small number of samples from the object to be detected.

A program in accordance with the present invention is a detection program for causing a computer to implement a process of detecting a candidate for a biomarker based on measurement data on a plurality of factors obtained in measurement on a biological object to be measured, the biomarker being an index of a symptom of the biological object, the program causing a computer to implement: the classification step of classifying factors into clusters based on a correlation of time-dependent changes of measurement data for each factor; the choosing step of choosing one of the clusters that satisfies choice conditions that are predetermined based on a correlation of time-dependent changes of measurement data for each factor and time-dependent changes of measurement data among different factors; and the detection step of detecting a factor in the chosen cluster as a candidate for a biomarker.

A detection program with these features, when run on a computer, enables the computer to operate as a detection device in accordance with the present invention. Therefore, the detection program is capable of detecting a biomarker candidate that serves as an early-warning signal indicating a pre-disease state that precedes a transition from a normal state to a disease state. If a biomarker is identified, the pre-disease state is detected by collecting only a small number of samples from the object to be detected.

Advantageous Effects of the Invention

The present invention enables diagnosis as to whether or not the subject to be diagnosed is in a pre-disease state, by collecting a biological sample from the subject to be diagnosed and examining whether or not there exists a biomarker that serves as an early-warning signal indicating a pre-disease state that immediately precedes a disease state in the collected biological sample. Therefore, the invention requires neither disease deterioration modeling nor identifying of a driving factor for the disease deterioration. The invention enables early diagnosis of a disease in a pre-disease state.

BRIEF DESCRIPTION OF DRAWINGS

FIG. 16 is a table of diagnosis data in a second validation example.

FIG. 17A is a graph representing exemplary time-dependent changes of the average standard deviation of a detected DNB candidate in the second validation example.

DESCRIPTION OF EMBODIMENTS

Figure 1:
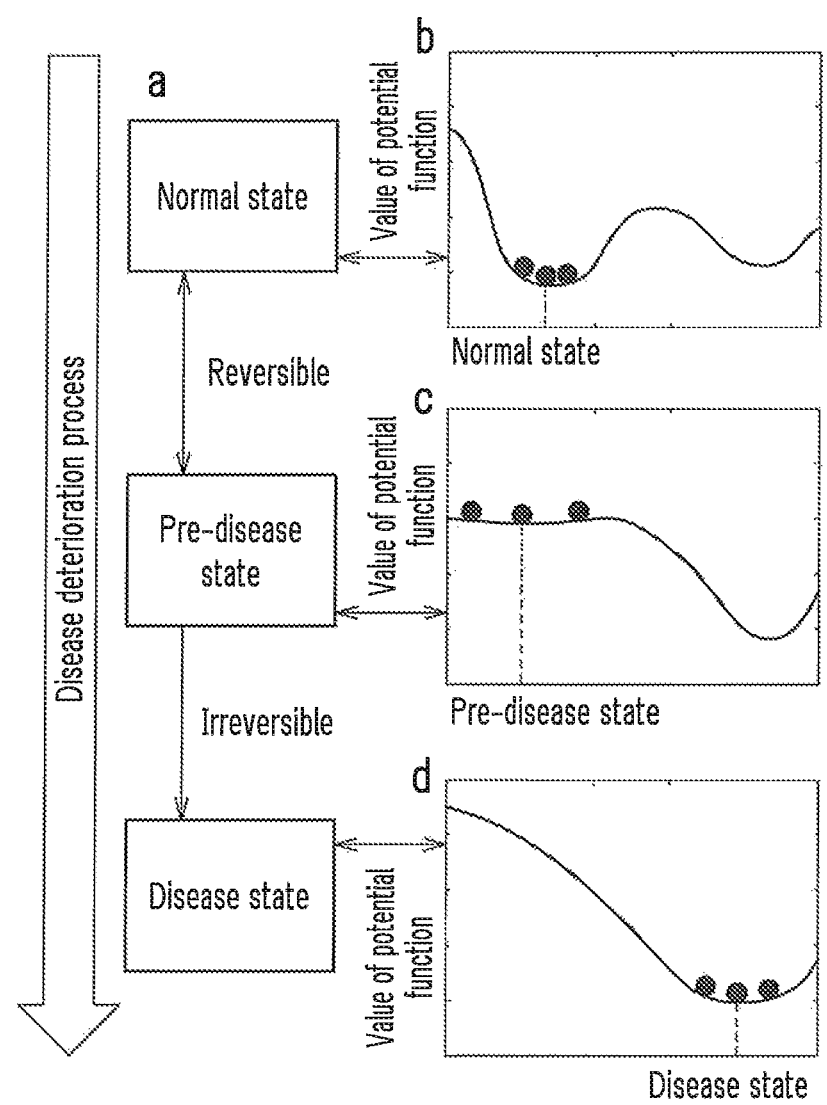
FIG. 1 is a schematic illustration of the progression process of a disease.

The inventors of the present invention have constructed a mathematical model of the chronological progression of a complex disease in accordance with the bifurcation process theory by genome high-throughput technology by which thousands of sets of information (i.e., high-dimensional data) can be obtained from a single sample, in order to study deterioration progression mechanisms of a disease at molecular network level. The study has revealed the existence of a dynamical network biomarker (DNB) with which an immediately preceding bifurcation (sudden deterioration) state before a critical transition can be detected in a pre-disease state. By using the dynamical network biomarker as an early-warning signal in a pre-disease state, a small number of samples enable an early diagnosis of a complex disease without disease modeling. The following will describe embodiments to implement the present invention based on a dynamical network biomarker.

Theoretical Principles

First, the theoretical principles of the present invention will be described. Assume that the progression of a disease can be expressed by the following dynamical system.

$$Z(k+1)=f(Z(k);P) \qquad \text{Eq. (1)}$$

$Z(k)=(z1(k), \ldots, zn(k))$ represent observed data, i.e., concentrations of molecules (e.g., gene expressions or protein expressions) at time k (k=0, 1, . . . ), e.g., hours or days, which are the variables describing the dynamical state of the system. P are parameters representing slowly changing factors, including genetic factors (e.g., SNP (single nucleotide polymorphism) and CNV (copy number variation)) and epigenetic factors (e.g., methylation and acetylation), which drive the system from one state (or attractor) to another.

The normal and disease states are described by respective attractors of the state equation $Z(k+1)=f(Z(k);P)$. Since the progression process of a complex disease has very complex dynamical features, the function f is a non-linear function with thousands of variables. Besides, the factor P, which drives system (1), is difficult to identify. It is therefore very difficult to formulate a system model for the normal and disease states for analysis.

To address these problems, the inventors of the present invention have focused on a critical transition state (i.e., a pre-disease state) of the system that immediately precedes a transition from the normal state to the disease state. System (1) generally has an equilibrium point that has the following properties:

1. $Z^*$ is a fixed point of system (1) such that $Z^*=f(Z^*;P)$
2. There is a value Pc such that one or a complex-conjugate pair of the eigenvalues of a Jacobian matrix, $\partial f(Z;Pc)/\partial Z|Z=Z^*$, equals 1 in modulus when P=Pc. Pc is a bifurcation threshold for the system.
3. When P≠Pc, the eigenvalue of system (1) are generally not 1 in modulus.

From these properties, the inventors have theoretically found that when system (1) has reached a critical transition state, specific features emerge. That is, when system (1) has reached a critical transition state, there emerges a dominant group (subnetwork) of some nodes of network (1) in which each node represents a different one of variables $z1, \ldots, zn$ of system (1). The dominant group that emerges in a critical transition state ideally has the following specific features:

(I) If both zi and zj are in the dominant group, then
 $PCC(zi,zj) \to \pm 1$;
 $SD(zi) \to \infty$; and
 $SD(zj) \to \infty$.
(II) If zi is in the dominant group, but zj is not, then
 $PCC(zi,zj) \to 0$;
 $SD(zi) \to \infty$; and
 $SD(zj) \to$ Bounded Value.
(III) If neither of zi nor zj is a node belonging to the dominant group,
 $PCC(zi,zj) \to \alpha, \alpha \in (-1,1) \setminus \{0\}$;
 $SD(zi) \to$ Bounded Value;
 $SD(zj) \to$ Bounded Value.

PCC(zi,zj) is a Pearson's correlation coefficient of zi with zj. SD(zi) and SD(zj) are standard deviations of zi and zj.

In other words, in network (1), the emerging dominant group with specific features (I) to (III) can be regarded as an indicator for a transition of system (1) to the critical transition state (pre-disease state). Therefore, the critical transition of system (1) can be detected by detecting the dominant group. In other words, the dominant group can be regarded as early-warning signals for the critical transition, that is, the pre-disease state that immediately precedes deterioration of a disease. In this manner, the pre-disease state can be identified by detecting only the dominant group which serves as early-warning signals, without directly coping with a mathematical model of system (1), no matter how complex system (1) becomes and even if the driving factor is unknown. The identifying of the pre-disease state enables precautionary measures and an early treatment of a disease.

The dominant group that can be early-warning signals in a pre-disease state is referred to as the "dynamical network biomarker" (hereinafter, abbreviated "DNB") in the present invention.

DNB Features and Identifying Conditions

As mentioned above, the DNB is a dominant group with a set of specific features (I) to (III) and emerges as a subnetwork of some of the nodes of network (1) when system (1) moves into the pre-disease state. If the nodes (z1, . . . , zn) in network (1) are the factors to be measured on biological molecules (e.g., genes, proteins, metabolites), the DNB is a group (subnetwork) of factors related to some of the biological molecules that satisfy specific features (I) to (III).

The conditions by which a DNB is identified may be specified based on specific features (I) to (III) as follows.

Condition (I): There exists a group of molecules, i.e., genes, proteins, or metabolites, whose average Pearson's correlation coefficients (PCCs) of molecules drastically increase in absolute value.

Condition (II): The average OPCCs of molecules between this group and any others (i.e., between molecules inside this group and any other molecules outside this group) drastically decrease in absolute value.

Condition (III): The average standard deviations (SDs) of molecules in this group drastically increase.

The group of biological molecules that simultaneously satisfy these DNB identifying conditions (I) to (III) are recognized to be a DNB.

Figure 2:
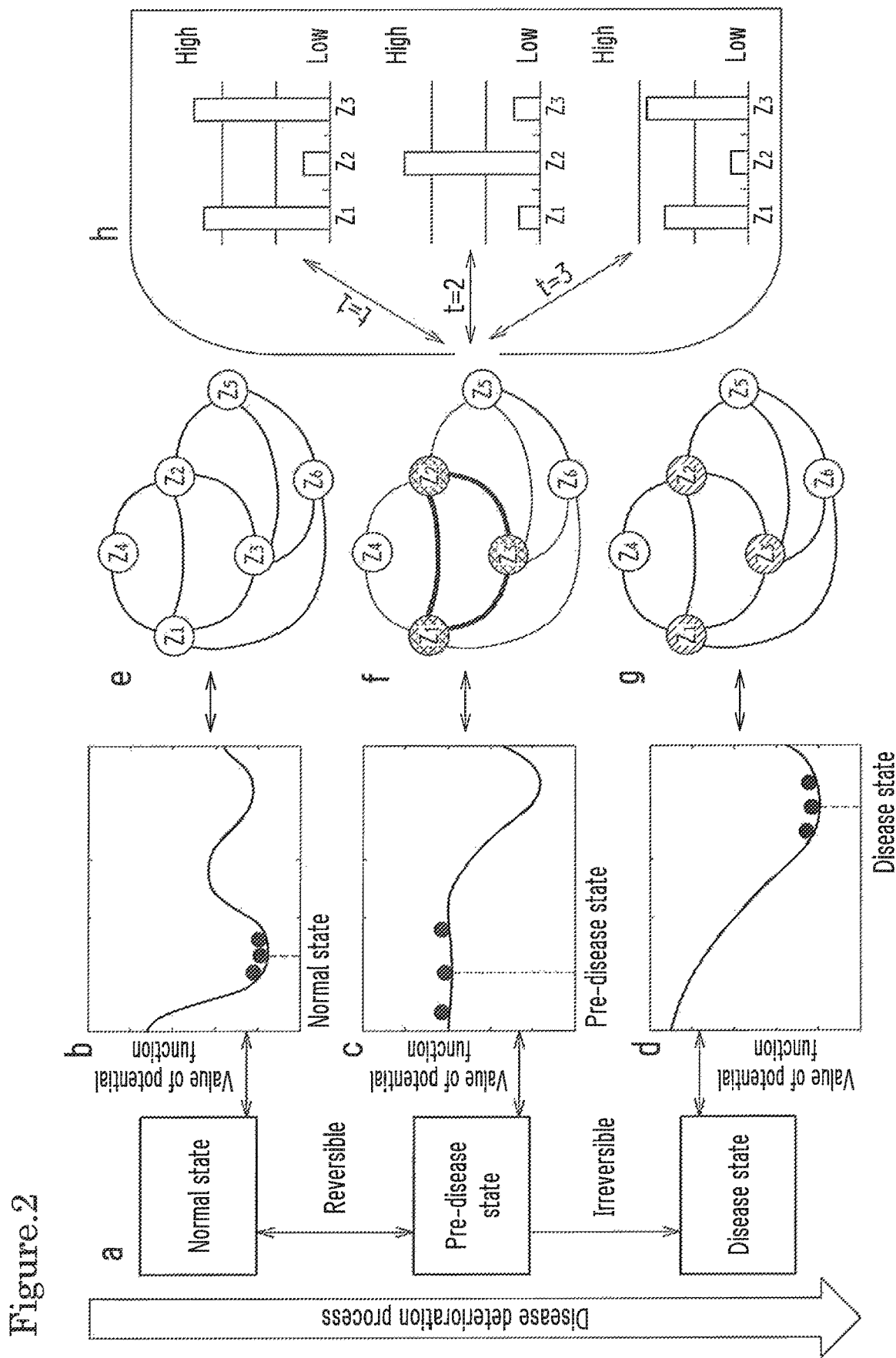
FIG. 2 is a schematic illustration of exemplary dynamical features of a DNB in accordance with a detection method of the present invention.

Next, the dynamical features of a DNB in a network will be described by taking a network of six nodes as an example to intuitively explain DNB features. FIG. 2 is a schematic illustration of exemplary dynamical features of a DNB in accordance with a detection method of the present invention. Portion a of FIG. 2 shows a normal state, a pre-disease state, and a disease state in a progression process of a disease.

Portions b, c, and d of FIG. 2 are conceptual graphical representations of stability of modeled system (1) by means of a potential function in the normal, pre-disease, and disease states during the course of disease progression. The horizontal axis indicates time, and the vertical axis indicates the value of the potential function. Portions e, f, and g of FIG. 2 are conceptual diagrams of exemplary states of the network for the system (1) that correspond respectively to the normal, pre-disease, and disease states. Portion h of FIG. 2 shows an example of temporal changes of molecule concentrations that serve as a DNB factor for the pre-disease state.

Nodes z1 to z6 represent factors for different kinds of biological molecules, for example, genes, proteins, and metabolites. The lines linking nodes z1 to z6 indicate correlations among the nodes. The thickness of the lines indicates the magnitude of a Pearson's correlation coefficient PCC. A pattern (or lack of it) in the circle surrounding z1 to z6 indicates the magnitude of the standard deviation SD of the node. Specifically, the standard deviation SD is a minimum when the circle contains no pattern and grows larger when the circle contains oblique lines in one direction, and grows even larger when the circle contains oblique lines in two directions.

The nodes in the normal state, as shown in e of FIG. 2, have equal and moderate correlations and standard deviation. In the pre-disease state, however, there emerges a group (z1 to z3) with notable specific features in comparison with the other nodes. Nodes z1 to z3 in the group, as shown in f of FIG. 2, drastically increase the Pearson's correlation coefficients among them and drastically decrease Pearson's correlation coefficients with the other nodes z4 to z6. Nodes z1 to z3 in the group increase the standard deviation among them. These phenomena are due to nodes z1 to z3 in the group undergoing drastic changes in concentration at different times (t=1, t=2, t=3) as shown in h of FIG. 2.

However, after a transition to the disease state, as shown in g of FIG. 2, nodes z1 to z3 in the group slightly increase the standard deviation among them, but the Pearson's correlation coefficients among them return uniformly to moderate values. In other words, the group (z1 to z3) has lost the specific features mentioned above.

As shown conceptually in FIG. 2, in the pre-disease state, there emerges a dominant group of some nodes with features unique to the pre-disease state. The emergence of such a dominant group, termed "DNB," is an early-warning signal indicating that the patient is in the pre-disease state and predicting that the patient could undergo a transition to the disease state, and may be used as a biomarker for an early diagnosis of the disease. In addition, unlike static biomarkers used in conventional diagnosis of a disease, the DNB is a subnetwork that emerges in a network in which features are changing. For these reasons, the dominant group is referred to as the DNB (dynamical network biomarker) in the present application.

Early-Warning Signal

As mentioned above, the DNB may be used as an early-warning signal indicating a pre-disease state for an early diagnosis of a disease. The strength of the early-warning signal can be measured by means of, for example, the average of the absolute values of the Pearson's correlation coefficients PCCs among the nodes in the DNB, the average of the absolute values of the Pearson's correlation coefficients OPCCs of the nodes in the DNB with other nodes, or the standard deviation SD of the DNB. Composite index I may be introduced that compositely reflects DNB features.

Composite index I, expressed by equation (2) below, is introduced as an example in the present invention.

$$I = SDd \times PCCd / OPCCd \quad \text{Eq. (2)}$$

In equation (2), PCCd is the average Pearson's correlation coefficient of the DNB in absolute value, OPCCd is the average Pearson's correlation coefficient of the nodes in the DNB with other nodes in absolute value, and SDd is the average standard deviation of the nodes in the DNB. As could be understood from equation (2), when SDd and PCCd increase, and OPCCd decreases, composite index I increases drastically and therefore enables highly sensitive detection of DNB features. Distance from the disease state can also be known to some extent from the value of composite index I.

Method for Detecting DNB

Figure 3:
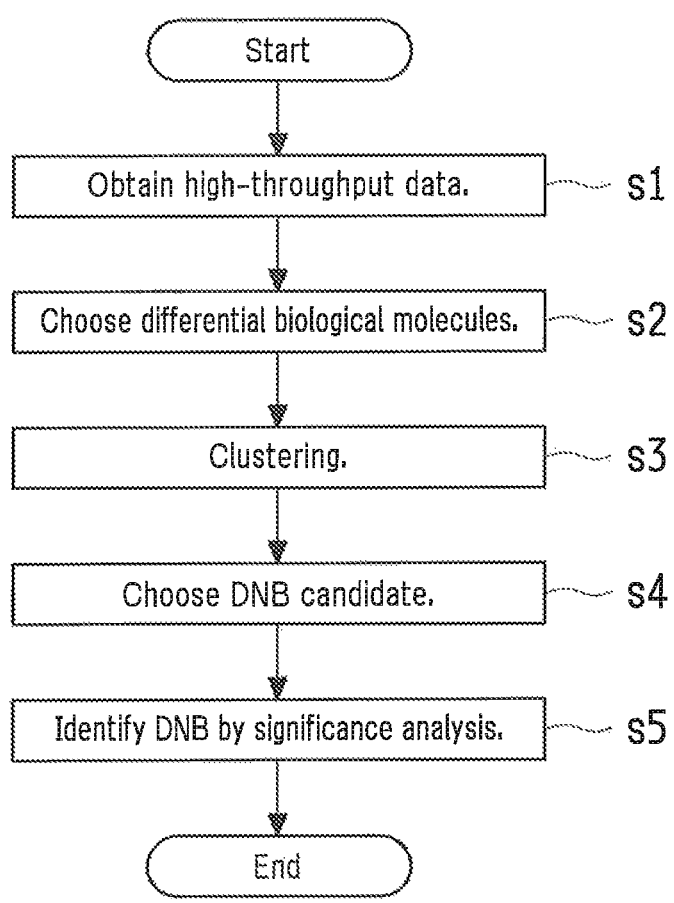
FIG. 3 is a flow chart depicting an exemplary method for detecting a DNB in accordance with an embodiment.

FIG. 3 is a flow chart depicting an exemplary method for detecting a DNB in accordance with an embodiment. In the method for detecting a DNB in accordance with the present invention, it is first of all necessary to obtain measurement data by measurement on a biological object. More than 20,000 genes can be measured on one biological sample by a DNA chip or like high-throughput technology. For statistical analysis, in the present invention, plural (six or more) biological samples are collected at different times from an object to be measured. Measurement is made on the collected biological samples, and the obtained measurement data is aggregated for statistical data. The method for detecting a DNB in accordance with the present invention, as illustrated in FIG. 3, primarily involves a process of obtaining high-throughput data (s1), a process of choosing differential biological molecules (s2), a process of clustering (s3), a process of choosing a DNB candidate (s4), and a process of identifying a DNB by significance analysis (s5). Next will be described each of these processes in detail.

Taking samples to be detected as case samples and reference samples as control samples, the process of obtaining high-throughput data in step s1 yields physiological data (measurement data (e.g., microarray data) on expressions of biological molecules) from the samples by high-throughput technology. A reference sample is, for example, a sample collected in advance from the patient who will undergo a medical checkup or a sample collected first during the course of collecting and is used as a control sample for the purpose of, for example, calibration of measuring instruments. A control sample is not essential, but useful to exclude error factors and improve measurement reliability.

Figure 4:
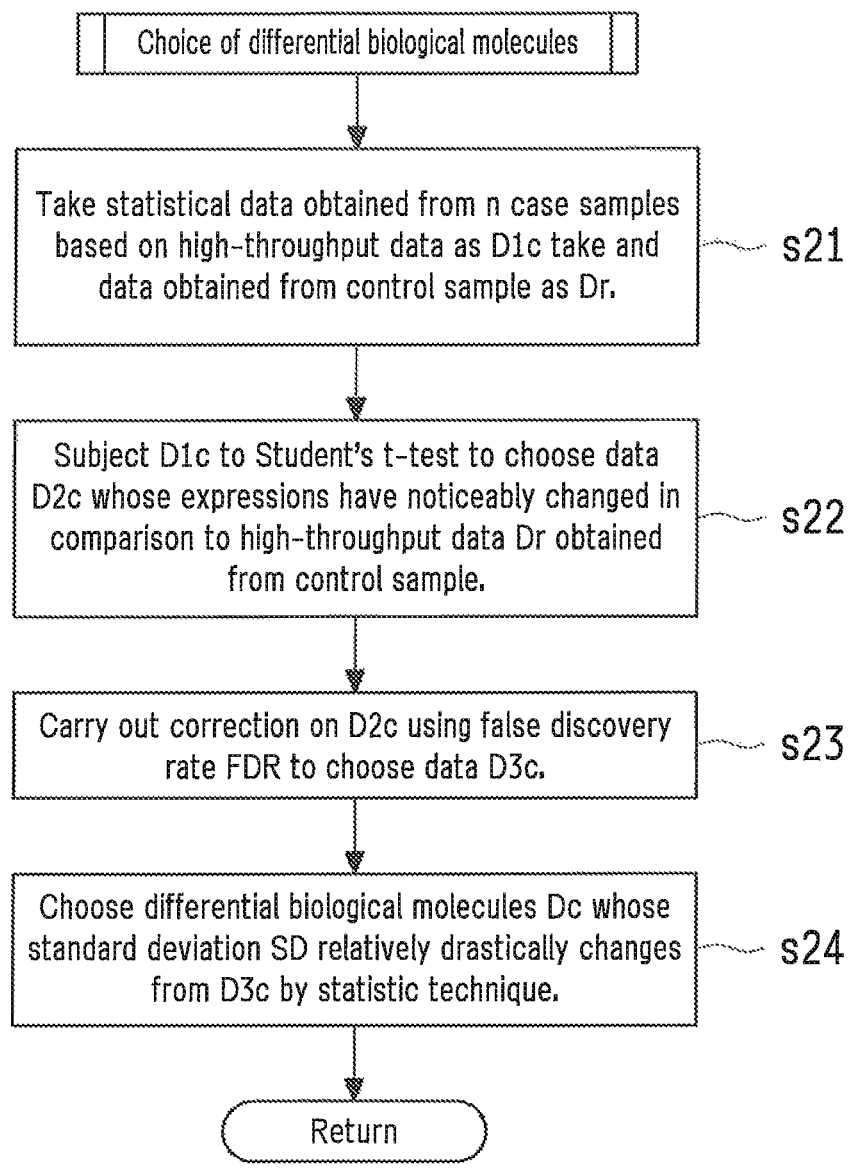
FIG. 4 is a flow chart depicting an exemplary process of choosing differential biological molecules in accordance with an embodiment.

The process of choosing differential biological molecules in step s2 chooses biological molecules whose expressions have noticeably changed. FIG. 4 is a flow chart depicting an exemplary process of choosing differential biological molecules in accordance with an embodiment. FIG. 4 shows in detail the process of choosing differential biological molecules in step s2 shown in FIG. 3.

As illustrated in FIG. 4, first, take statistical data obtained from n case samples based on high-throughput data (expressions of biological molecules) as $D1c$ and data obtained from control samples as Dr (s21). Next, the biological molecules $D1c$ from the case samples are subjected to a Student's t-test to choose biological molecules $D2c$ whose expressions have noticeably changed in comparison to the high-throughput data Dr obtained from the control samples (s22). Student's t-test is an exemplary technique to choose biological molecules $D2c$ whose expressions have noticeably changed in step s22; the technique is however by no means limited in any particular manner. Another test, such as the Mann-Whitney U test, may be used. Tests by such a non-parametric technique are especially effective when the population D1c does not follow a normal distribution. In addition, in Student's t-tests, the significance level a may be set, for example, to 0.05, 0.01, or another appropriate value.

Next, multiple comparisons or multiple Student's t-tests are corrected for the biological molecules D2c from the case samples using a FDR (false discovery rate) to choose corrected case sample gene or protein data D3c (s23). Next, Dc whose standard deviation SD relatively drastically changes are chosen as differential biological molecules from the corrected case sample gene or protein data D3c by a two-fold change method. The chosen differential biological molecules Dc not only have a noticeable difference from the biological molecules Dr obtained from the control samples, but also greatly deviate from their own average value. In step s23, Student's t-test is again not the only feasible test technique.

Next, the process of clustering (s3 in FIG. 3) is carried out. The process of clustering in this context is a process by which multiple biological molecules are classified into groups of mutually closely correlated molecules. Each of the groups into which biological molecules are classified is called a cluster. In other words, closely correlated biological molecules are in a single cluster. The differential biological molecules Dc chosen in step s24, shown in FIG. 4, are classified into n clusters. All the obtained clusters are potential dominant groups, that is, DNB candidates that should be detected.

Figure 5:
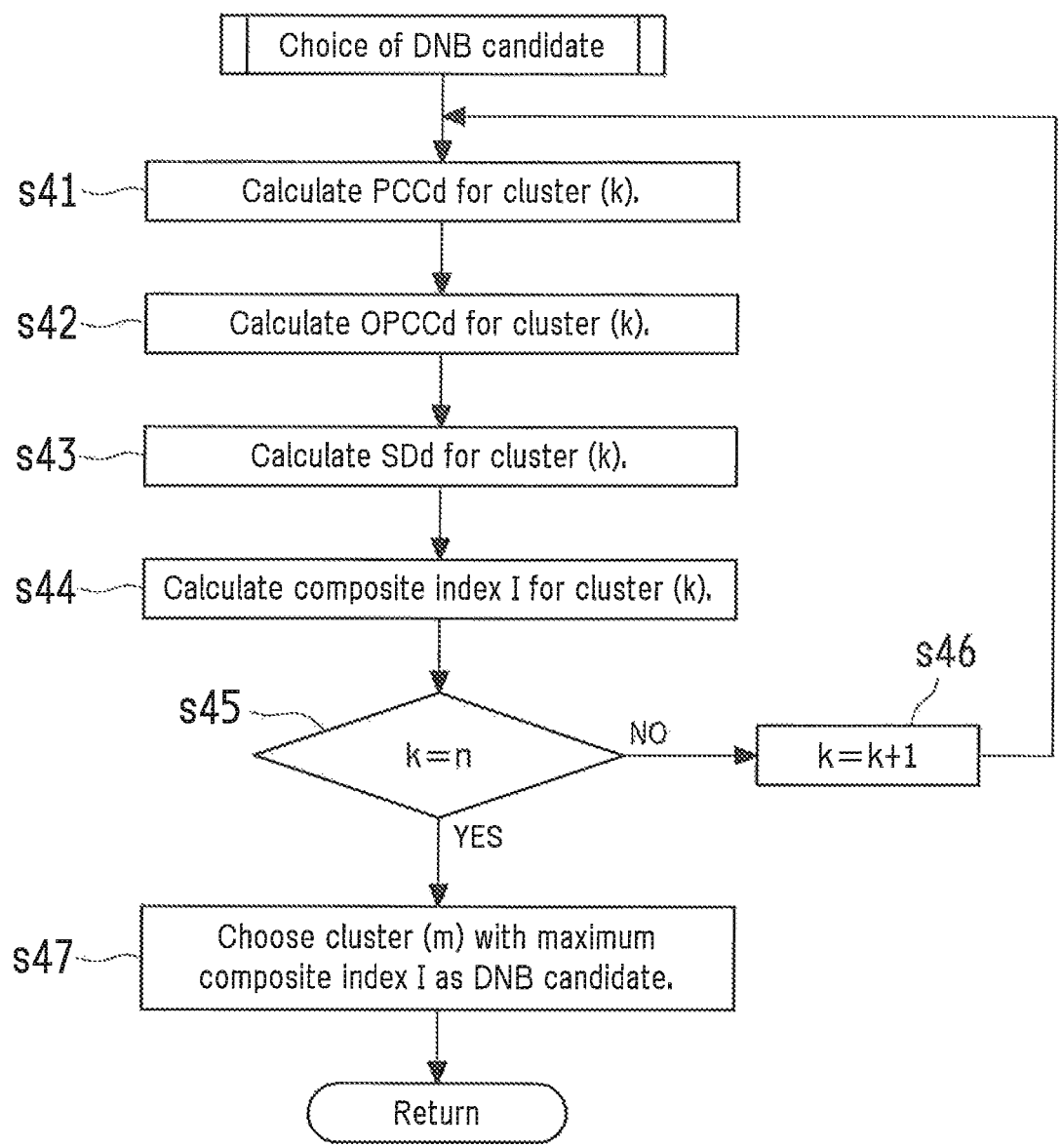
FIG. 5 is a flow chart depicting an exemplary process of choosing a DNB candidate in accordance with an embodiment.

Next, the process of choosing a DNB candidate (s4) shown in FIG. 3 is carried out. FIG. 5 is a flow chart depicting an exemplary process of choosing a DNB candidate in accordance with an embodiment. FIG. 5 shows in detail the process of choosing a DNB candidate in step s4 shown in FIG. 3. In other words, the process of choosing a DNB candidate is carried out in accordance with the flow chart for the process of choosing a DNB candidate shown in FIG. 5. In the circulation loop shown in FIG. 5, the average PCCd(k) of the absolute values of Pearson's correlation coefficients among the nodes in the same cluster, the average OPCCd(k) of the absolute values of Pearson's correlation functions of the nodes in each cluster with the other nodes, the average SDd(k) of standard deviations of the nodes in each cluster, and the composite index I(k) are calculated for all clusters (k) (k=1, . . . , n) (s41 to s46). A cluster with a maximum composite index I value is chosen as a DNB candidate from all the clusters (s47).

Figure 6:
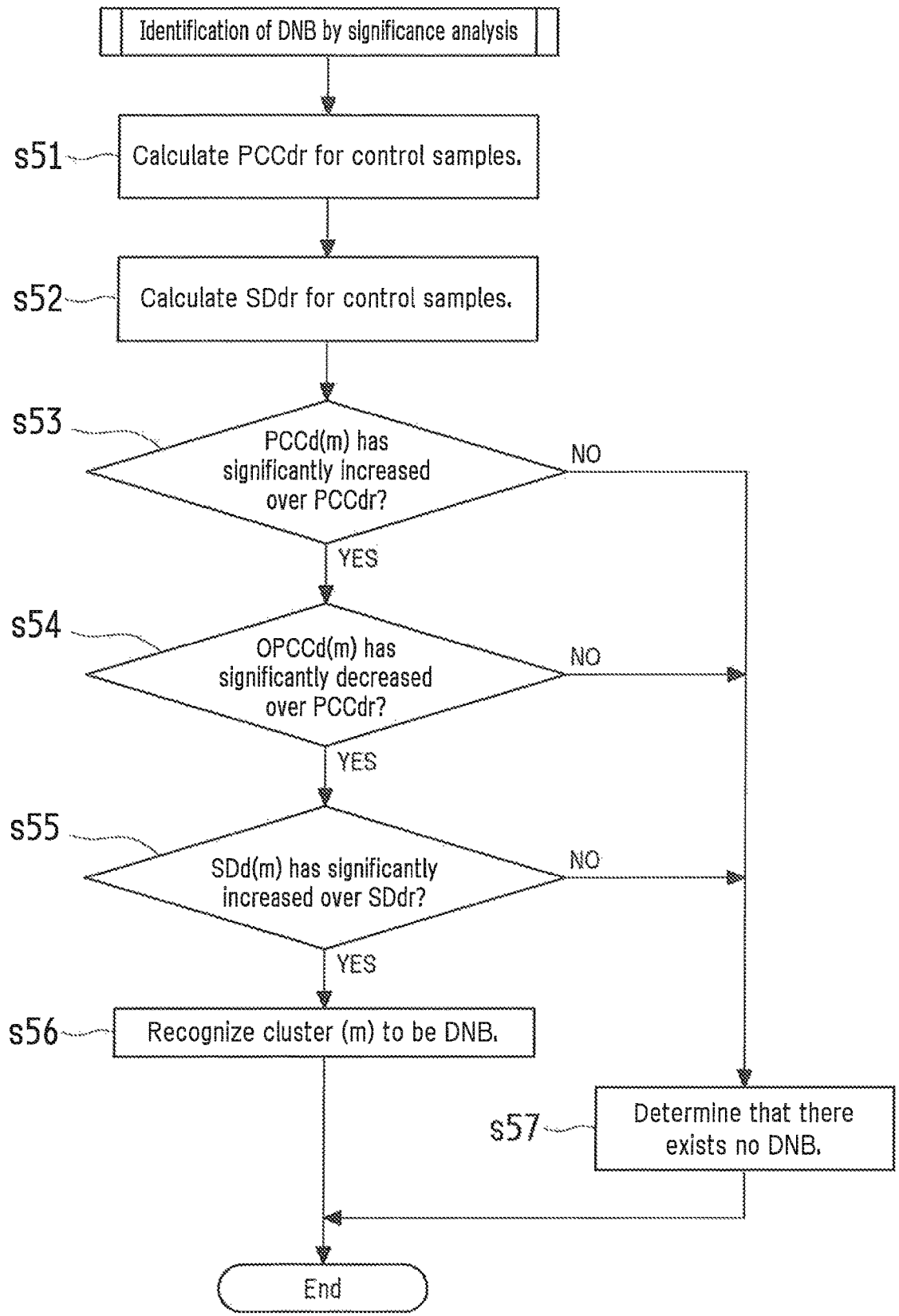
FIG. 6 is a flow chart depicting an exemplary process of identifying a DNB in accordance with an embodiment.

Next, the process of identifying a DNB by significance analysis (s5 in FIG. 3) shown in FIG. 3 is carried out. FIG. 6 is a flow chart depicting an exemplary process of identifying a DNB in accordance with an embodiment. FIG. 6 shows in detail the process of identifying a DNB by significance analysis in step s5 in FIG. 3. In other words, it is determined whether or not the cluster (m) chosen as a DNB candidate in step s47 is a DNB in accordance with DNB identifying conditions (I) to (III) explained above. Various significance analyses are applicable for the identification. The process is carried out, as an example, in accordance with the flow chart of the process of identifying a DNB shown in FIG. 6.

As illustrated in FIG. 6, first, the average PCCdr of the absolute values of Pearson's correlation coefficients of data obtained from the control samples among the nodes and the average SDdr of standard deviations of the nodes are calculated (s51, s52). It is then determined whether or not the average PCCd(m) of the absolute values of Pearson's correlation coefficients among the nodes in the cluster (m) chosen in step s47 has significantly increased over the average PCCdr of the Pearson's correlation coefficients of the control samples (s53). If it is determined that the average PCCd(m) has not significantly increased (No), a result that there exists no DNB is output (s57), and the process is ended. On the other hand, if it is determined that the average PCCd(m) has significantly increased (Yes), the process proceeds to step s54. In step s54, it is determined whether or not the average OPCCd(m) of Pearson's correlation coefficients of the nodes in the cluster (m) with other nodes has significantly decreased over the average PCCdr of Pearson's correlation coefficients of the control samples (s54). If it is determined that the average OPCCd(m) has not significantly decreased (No), a result that there exists no DNB is output (s57), and the process is ended. On the other hand, if it is determined that the average OPCCd(m) has significantly decreased (Yes), the process proceeds to step s55. In step s55, it is determined whether or not the average standard deviation SDd(m) of the nodes in the cluster (m) has significantly increased over the average standard deviation SDr of the control samples. If it is determined that the average standard deviation SDd(m) has not significantly increased (No), it is determined that there exists no DNB (s57), and the process is ended. On the other hand, if the average standard deviation SDd(m) has significantly increased, the cluster (m) is recognized to be a DNB (s56), and the process is ended.

Method of Early Diagnosis of Disease by DNB

Figure 7:
FIG. 7 is a diagram representing an exemplary diagnosis schedule by a DNB-based early diagnosis of a disease in accordance with an embodiment.

A desirable diagnosis schedule may include multiple diagnoses with certain intervals, with a couple of samples being collected in each diagnosis. FIG. 7 is a diagram representing an exemplary diagnosis schedule by a DNB-based early diagnosis of a disease in accordance with an embodiment. As illustrated in FIG. 7, samples are collected in multiple periods (period-1, period-2, . . . , and period-T). Generally, six or more samples are preferably collected in each period to ensure accuracy of data. The interval between two consecutive periods may be set to days, weeks, months, or even longer (e.g., years), depending on the condition of the disease. In each period, samples are preferably collected at different points in time in a short period of time. For example, six samples are collected at six points in time in one day. The intervals between points in time may be set, for example, to minutes or hours depending on the situation.

Figure 8:
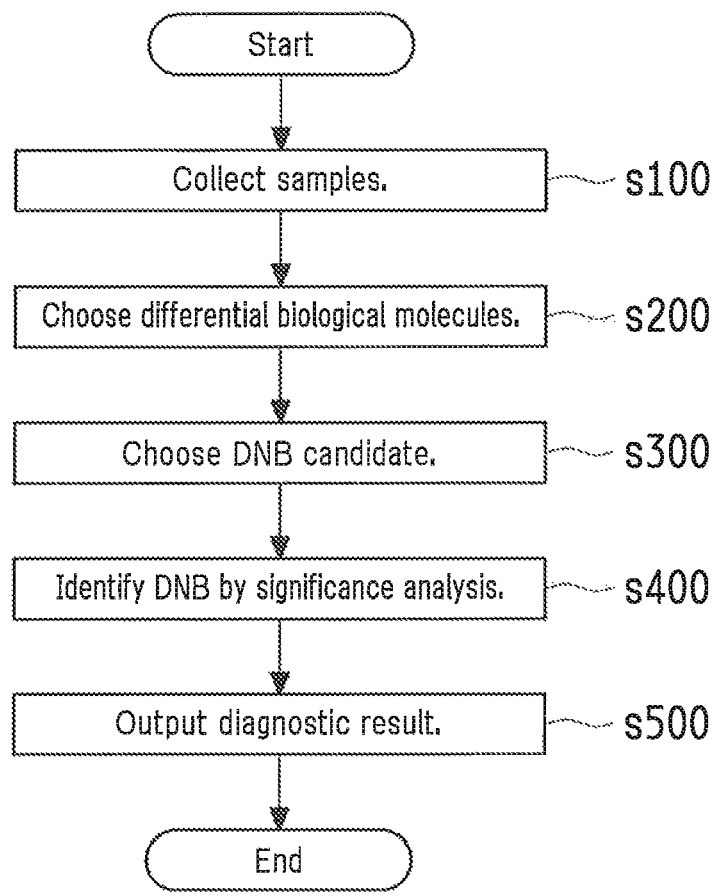
FIG. 8 is a flow chart depicting an exemplary DNB-based early diagnosis of a disease in accordance with an embodiment.

FIG. 8 is a flow chart depicting an exemplary DNB-based early diagnosis of a disease in accordance with an embodiment. As illustrated in FIG. 8, the method of early diagnosis of a disease by a DNB primarily involves a process of collecting samples (s100), a process of choosing differential biological molecules (s200), a process of choosing a DNB candidate (s300), a process of identifying a DNB by significance analysis (s400), and a process of outputting diagnostic results (s500). Next, these processes will be concretely described in detail.

Process of collecting samples (s100): Samples from which necessary physiological data are to be acquired are collected according to the disease to be diagnosed in the same manner as in general disease diagnosis. For example, in the case of a liver disease, blood and liver tissue samples are collected.

In a diagnosis, in addition to taking samples collected from a subject to be diagnosed as case samples, samples collected from a healthy person who is not a subject to be diagnosed may be taken as reference samples, and samples collected first from a subject to be diagnosed may be taken as control samples.

Process of choosing differential biological molecules (s200): Differential biological molecules are chosen from samples collected in step s100 according to the flow chart for the process of choosing differential biological molecules shown in FIG. 4.

Process of choosing DNB candidate (s300): A dominant group, which would be a DNB candidate, is chosen from the differential biological molecules chosen in step s200 according to the flow chart for DNB candidate choice shown in FIG. 5.

Process of identifying DNB by significance analysis (s400): It is determined, according to the flow chart depicting a method of identifying a DNB by significance analysis shown in FIG. 6, whether or not the DNB candidate chosen in step s300 is a DNB.

Process of outputting diagnostic results (s500): If it is determined in step s400 that there exists no DNB, the data on the DNB candidate chose in step s300 is recorded in a memory device as reference data for a next diagnosis, and a diagnostic result that there exists no abnormality is output. On the other hand, if it is determined in step s400 that there exists a cluster recognized as a DNB, the biological molecule data of the recognized cluster is recorded as a member of a DNB, and a diagnostic result that the patient is in a pre-disease state is output. In addition, a diagnostic result related to the detected DNB may be output. The diagnostic result in this context may be a result that gives useful information for a physician to diagnose a disease. In other words, the diagnostic result output in step s500 is not a diagnosis per se by the physician, but output data that gives useful information for diagnosis to assist diagnosis by a physician.

For example, as a diagnostic result, composite index I, compositely reflecting the DNB features, may be output. A higher composite index I indicates increasing proximity to a tipping point. Greater warning effect is achieved if the output is given in graphic form from which one can intuitively see disease risk in proportion to composite index I.

Figure 9:
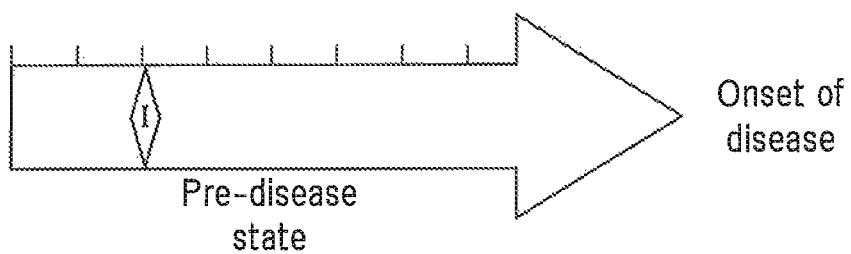
FIG. 9 is an exemplary graphic showing a disease risk in proportion to composite index I.
Figure 10:
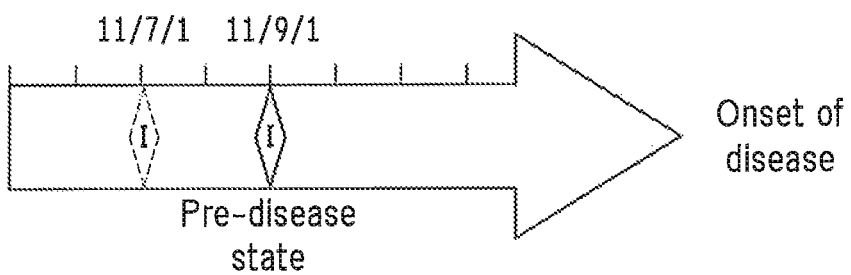
FIG. 10 is an exemplary graphic showing a disease risk in proportion to composite index I.

FIGS. 9 and 10 are exemplary graphics showing disease risk in proportion to composite index I. In FIG. 9, the arrow as a whole represents the pre-disease state, and the flow in the direction indicated by the arrow represents time-dependent changes of the disease (onset of the disease). The rhombus sign toward the left inside the arrow is an onset risk pointer that changes its location depending on the composite index I value obtained in a diagnosis. The rhombus sign approaches the right end of the arrow with a higher composite index I value.

If the patient has ever undergone an early diagnosis of a disease by a DNB, disease risk may be shown in proportion to composite index I as in FIG. 10, along with the composite index obtained in the last diagnosis. In FIG. 10, the rhombus sign drawn in dotted lines indicates the composite index obtained in a diagnosis on Jul. 1, 2011, while the rhombus sign drawn in solid lines indicates the composite index obtained in a diagnosis on Sep. 1, 2011. It is intuitively determined from the change in location of the rhombus sign that the patient is approaching the disease state.

Maps (see, e.g., FIG. 15 below) showing the entire network including the detected DNB or a part of the network including the DNB may be output as information related to the DNB.

A list of biological molecules that are DNB members may be output. As mentioned above, a DNB emerges in a pre-disease state when a transition from a normal state to a disease state occurs. The biological molecules per se, that is, genes, proteins, or metabolites, detected as a DNB however are not necessarily pathologic genes, proteins, or metabolites that are a disease progression factor. It is known that some DNB members are related to the disease.

Therefore, if the biological molecules (genes, proteins, or metabolites), included in the detected DNB members, that are related to a particular disease are extracted, for example, a physician can through a diagnosis learn to some extent of a disease whose symptoms could possibly be developed by a patient or subject to be diagnosed.

Therefore, subsequent to the output of a diagnostic result (s500 in FIG. 8), genes, proteins, or metabolites that are related to a disease may be extracted from the detected DNB by using a database of correspondence of genes, proteins, or metabolites and diseases and output as a diagnostic result which aids a diagnosis.

If, for example, a DNB is detected in the data on genes, proteins, or metabolites obtained from blood collected from the person who is to undergo a medical checkup, that output offers some help in identifying a disease related to the genes, proteins, or metabolites included in the DNB. Potential diseases of the patient to be diagnosed can hence be diagnosed in an early stage.

Detection Device

Figure 11:
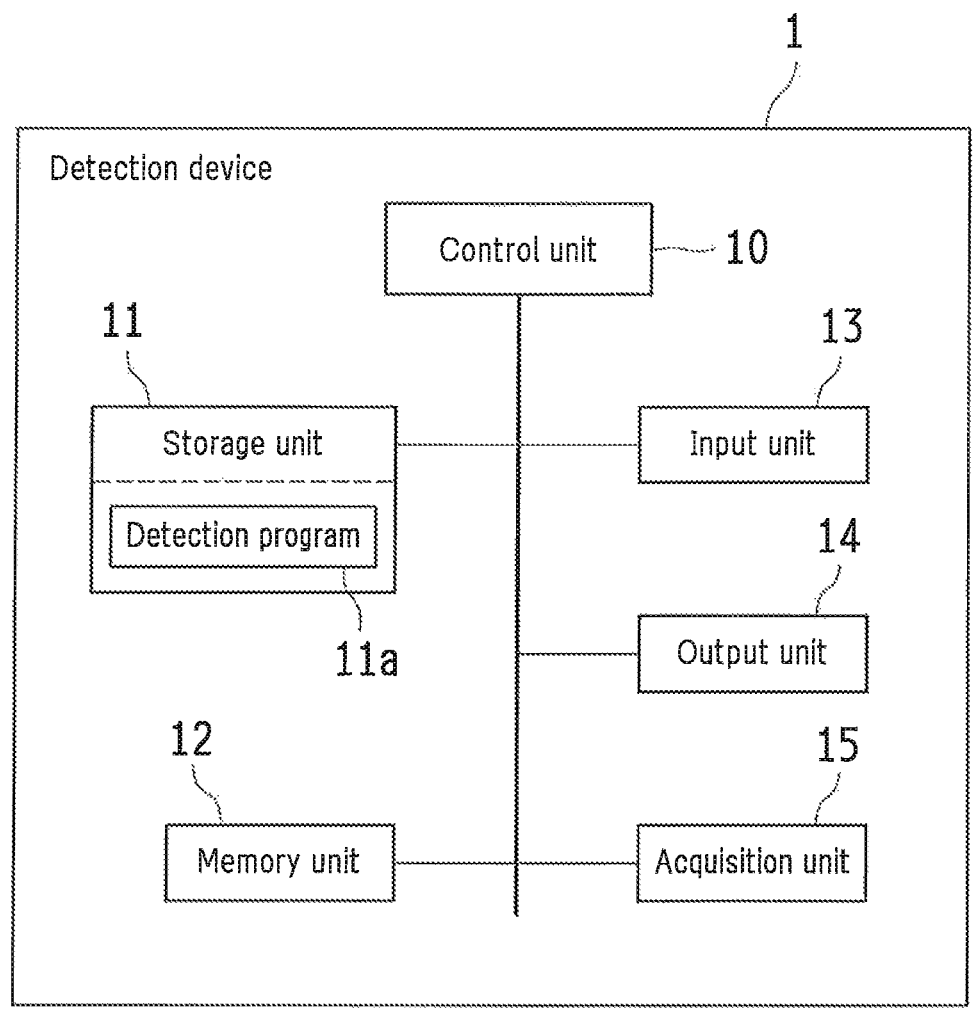
FIG. 11 is a block diagram illustrating an exemplary configuration of a detection device in accordance with the present invention.

The method for detecting a DNB described in detail above may be implemented by a computer-based detection device, which is another embodiment of the present invention. FIG. 11 is a block diagram illustrating an exemplary configuration of a detection device in accordance with the present invention. A detection device 1 shown in FIG. 11 may be realized using a personal computer, a client computer connected to a server computer, or any other kind of computer. The detection device 1 includes, for example, a control unit 10, a storage unit 11, a memory unit 12, an input unit 13, an output unit 14, and an acquisition unit 15.

The control unit 10 is composed using a CPU (central processing unit) and other circuitry and is a mechanism controlling the whole detection device 1.

The storage unit 11 is a non-volatile auxiliary storage mechanism, such as a HDD (hard disk drive) or a like magnetic storage mechanism or a SSD (solid state disk) or a like non-volatile semiconductor storage mechanism. The storage unit 11 stores a detection program 11a in accordance with the present invention and other various programs and data.

The memory unit 12 is a volatile main memory mechanism, such as a SDRAM (synchronous dynamical random access memory) or a SRAM (static random access memory).

The input unit 13 is an input mechanism including hardware (e.g., a keyboard and a mouse) and software (e.g., drivers).

The output unit 14 is an output mechanism including hardware (e.g., a monitor and a printer) and software (e.g., drivers).

The acquisition unit 15 is a mechanism that externally acquires various data: specifically, various hardware, such as a LAN (local area network) port for acquiring data over a communications network, parallel cables to be connected to measuring instruments, and ports to be connected to dedicated lines, and software, such as drivers.

By loading the detection program 11a stored in the storage unit 11 into the memory unit 12 and running the detection program 11a under the control of the control unit 10, the computer implements various procedures stipulated in the detection program 11a to function as the detection device 1 in accordance with the present invention. The storage unit 11 and the memory unit 12, despite being separately provided for the sake of convenience, have similar functions of storing various information; which of the mechanisms should store which information may be determined in a suitable manner according to device specifications, usage, etc.

Figure 12:
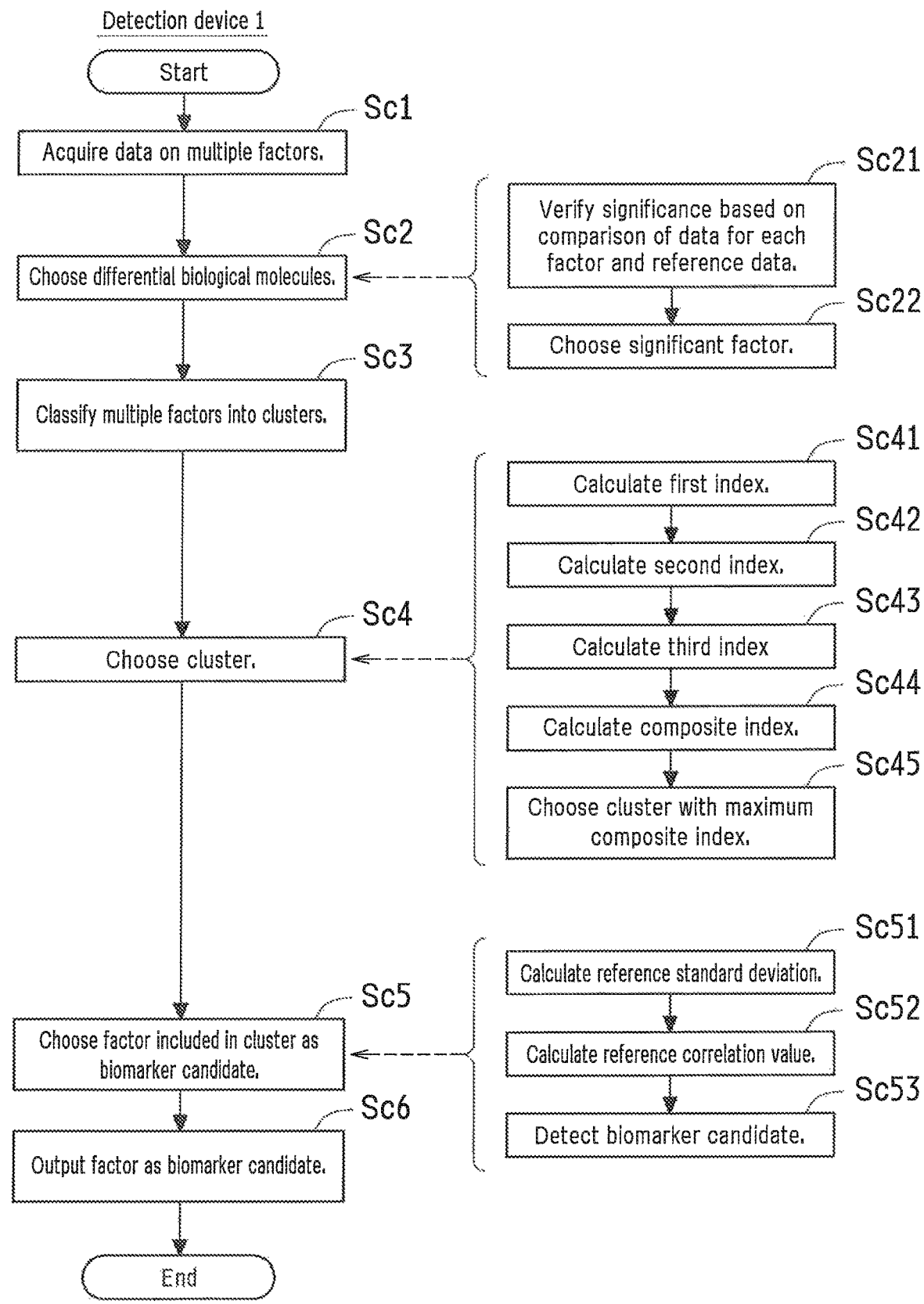
FIG. 12 is a flow chart depicting an exemplary process of detecting a DNB as implemented by a detection device in accordance with the present invention.

FIG. 12 is a flow chart depicting an exemplary process of detecting a DNB as implemented by the detection device 1 in accordance with the present invention. The detection device 1 in accordance with the present invention implements the aforementioned process of detecting a DNB. The control unit 10 in the detection device 1 acquires, through the acquisition unit 15, measurement data on a plurality of factors obtained by measurement on a biological object (Sc1). Step Sc1 corresponds to the process of obtaining high-throughput data indicated by step s1 in FIG. 3. Note that although the term "factor" is used in this context to indicate that it is an object for computer processing, the "factor" here refers to a gene-related measured item, a protein-related measured item, a metabolite-related measured item, or another measured item that could be a node for a DNB. An image-related measured item may be used that is obtained from, for example, a CT scan image of the interior of the body or a like image output of a measuring instrument.

The control unit 10 verifies whether or not each measurement data set obtained for a factor has significantly changed with time and chooses differential biological molecules based on a result of the verification (Sc2). Step Sc2 corresponds to the process of choosing differential biological molecules indicated by step s2 in FIG. 3.

Therefore, in step Sc2, the control unit 10 verifies significance based on a result of comparison of the measurement data for each factor and the reference data predetermined for each factor and each time series (Sc21) and chooses a factor that is verified to have significantly changed with time (Sc22). In other words, the steps shown in FIG. 4 are implemented in step Sc2. The data processed as reference data by the detection device 1 is control samples. For example, the detection device 1 is set up to take samples that are obtained first as control samples to handle the samples as reference data based on this setup.

The control unit 10 classifies factors into clusters based on a correlation of the time-dependent changes of measurement data on each chosen factor (Sc3). Step Sc3 corresponds to the process of clustering indicated by step s3 in FIG. 3.

The control unit 10 chooses one of the classified clusters that satisfies choice conditions that are predetermined based on a correlation of the time-dependent changes of measurement data for each factor and the time-dependent changes of measurement data among different factors (Sc4). Step Sc4 corresponds to the process of choosing a DNB candidate indicated by step s4 in FIG. 3.

Therefore, in step Sc4, for each cluster, the control unit 10 calculates, as a first index, the average of values representing a correlation of the measurement data for each factor in the cluster (Sc41), calculates, as a second index, the average of values representing a correlation among measurement data on a factor inside the cluster and measurement data on a factor outside the cluster (Sc42), and calculates, as a third index, the average standard deviation of measurement data for each factor in the cluster (Sc43). In step Sc4, the control unit 10 further calculates a composite index based on a product of the first index, the second index, and a reciprocal of the third index (Sc44) and chooses one of the clusters that has a maximum composite index (Sc45). In other words, the steps shown in FIG. 5 are implemented. The first index, the second index, the third index, and the composite index may be, for example, the average PCCd(k) of the absolute values of Pearson's correlation coefficients among the nodes in the cluster, the average OPPCd(k) of the absolute values of Pearson's correlation functions of the nodes in the cluster with other nodes, the average SDd(k) of standard deviations of the nodes in the cluster, and the composite index I(k).

The control unit 10 detects a factor included in the chosen cluster as a biomarker candidate (Sc5). Step Sc5 corresponds to the process of identifying a DNB indicated by step s5 in FIG. 3.

Therefore, in step Sc5, for each factor, the control unit 10 calculates a reference standard deviation representing the average standard deviation of the corresponding reference data (Sc51) and calculates a reference correlation value representing the average of values representing correlations among different factors (Sc52). Also in step Sc5, if the first index has significantly increased over the reference standard deviation, the second index has significantly decreased over the reference correlation value, and the third index has significantly increased over the reference standard deviation, the item included in the cluster is detected as a biomarker (Sc53). In other words, the steps shown in FIG. 6 are implemented. The reference standard deviation and the reference correlation value may be, for example, the average PCCdr of the absolute values of Pearson's correlation coefficients among the nodes and the average SDdr of standard deviations of the nodes.

The control unit 10 outputs the factor detected as a biomarker candidate from the output unit 14 (Sc6), and the process is ended.

First Validation Example

The accuracy of diagnosis by the method of DNB-based early diagnosis of a disease in accordance with the present invention was validated in the following manner. A diagnosis was performed according to the diagnosis method in accordance with the present invention by using experimental data obtained from mice with a lung disorder. The diagnostic result was then compared with the actual disease progression to validate effectiveness of the diagnosis method in accordance with the present invention. Next, this validation example will be described in detail. The experimental data was obtained in experiments that examined the molecular level mechanism of acute lung injury caused by inhalation of carbonyl chloride. In the experiment, (i) multiple experimental CD-1 male mice were divided into a case group and a control group, (ii) the case group was kept in a normal air environment, and the control group was kept in an air environment containing carbonyl chloride (poisonous gas), and (iii) the health condition of the mice of the two groups was observed. The health condition of mice in the case group being exposed to carbonyl chloride was diagnosed according to the diagnosis method in accordance with the present invention by using the experimental data. Typically, mice develop a carbonyl chloride-induced lung disorder after inhaling a certain amount of carbonyl chloride.

Figures 13, 14A:
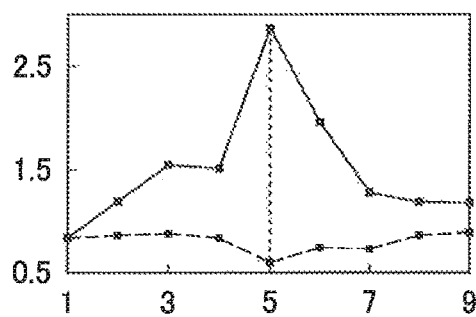
FIG. 13 is a table of data for diagnostic use for a first validation example.
FIG. 14A is a graph representing exemplary time-dependent changes of the average standard deviation of a DNB candidate detected in the first validation example.

FIG. 13 is a table of data for diagnostic use for the first validation example. As illustrated in FIG. 13, the subjects to be diagnosed were mice (CD-1 male mice) with a carbonyl chloride-induced lung disorder. Samples were collected from lung tissues of the mice in the case group (subjects) and those in the control group (referents). Sampling points were 0, 0.5, 1, 4, 8, 12, 24, 48, and 72 hours into the experiment. There were 22,690 genes used to detect a DNB.

Specifically, the following processes were carried out according to the diagnosis method in accordance with the present invention.

Differential expression genes were chosen from the high-throughput gene data for acute lung injury. At each sampling point (or period), there are six case samples and six control samples. At the 0 h sampling point, the case samples were considered to be identical to the control samples.

At each sampling point, by using the student t-test with significance level p<0.05, A=[0, 53, 184, 1,325, 1,327, 738, 980, 1,263, 915] differential expression molecules were selected.

Based on set A of the selected differential expression molecules, by using the false discovery rate (FDR) and by two-fold change screening, B=[0, 29, 72, 195, 269, 163, 173, 188, 176] genes were obtained respectively for the 9 sampling time points.

For the selected gene set B in the above step, molecules were clustered at each sampling time point by correlations. For each sampling point, 40 clusters were obtained.

At each sampling point, a new type of data normalization was conducted for all genes in the 40 clusters. At each sampling point, for every normalized cluster or group, the average standard deviation (SDd, third index), average Pearson's correlation coefficient (|PCC| in absolute value, second index) of the cluster members, average OPCCd (first index) between the cluster members and other genes, and the composite index I were calculated.

One of the clusters that had a maximum composite index I in the calculated case group was chosen as a DNB candidate at each sampling point. It was determined whether or not the DNB candidate was a DNB by significance analysis, with the average SDc of standard deviations of the control group and the average PCCc of the absolute values of Pearson's correlation coefficients among genes being used as the standards. As a result, the number of clusters that were DNBs was 0, 0, 0, 0, 1, 0, 0, 0, and 0 at the respective sampling points.

In other words, a DNB was detected at the fifth sampling point (8 h), and the DNB is the 111-th cluster with 220 genes.

Figure 14B:
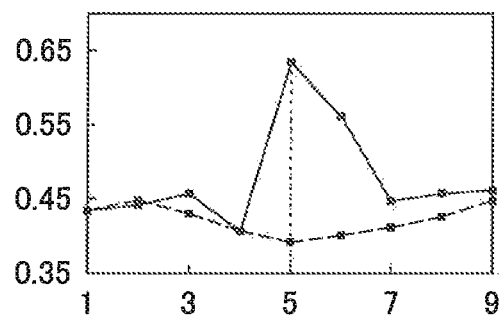
FIG. 14B is a graph representing exemplary time-dependent changes of the average of the absolute values of Pearson's correlation coefficients among cluster members that are detected DNB candidates in the first validation example.
Figure 14C:
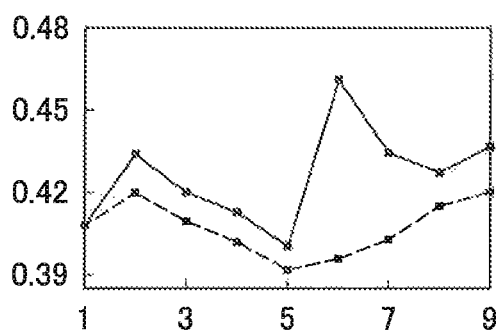
FIG. 14C is a graph representing exemplary time-dependent changes of the average of the absolute values of Pearson's correlation coefficients of cluster members that are detected DNB candidates with other genes in the first validation example.
Figure 14D:
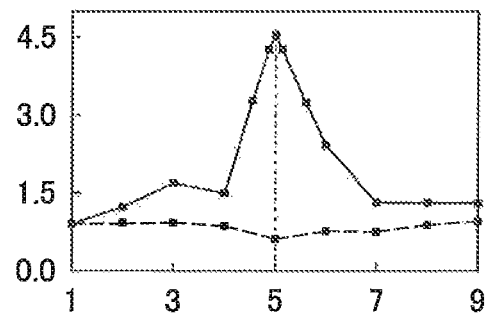
FIG. 14D is a graph representing exemplary time-dependent changes of the average of composite indices for a detected DNB candidate in the first validation example.

FIG. 14A is a graph representing exemplary time-dependent changes of the average SDd of standard deviations of a DNB candidate detected in the first validation example. FIG. 14B is a graph representing exemplary time-dependent changes of the average PCCd of the absolute values of Pearson's correlation coefficients among cluster members that are detected DNB candidates in the first validation example. FIG. 14C is a graph representing exemplary time-dependent changes of the average OPCCd of the absolute values of Pearson's correlation coefficients of cluster members that are detected DNB candidates with other genes in the first validation example. FIG. 14D is a graph representing exemplary time-dependent changes of composite index I for a detected DNB candidate in the first validation example. In FIGS. 14A to 14D, the horizontal axis indicates time periods t, and the vertical axis indicates respectively the average SDd of standard deviations (FIG. 14A), the average PCCd of the absolute values of Pearson's correlation coefficients among the members of the cluster (FIG. 14B), the average OPCCd of the absolute values of Pearson's correlation coefficients of the members of the cluster with other genes (FIG. 14C), and the composite index I (FIG. 14D). Broken lines represent time-dependent changes of various indices that are DNB candidates detected in the case group. Solid lines represent time-dependent changes of various indices for one cluster chosen from the control group.

As understood from FIGS. 14A to 14D, the first index PCCd, the third index SDd, and the composite index I of the DNB candidate started to increase drastically in the fourth time period (i.e., 4 h) and peaked in the fifth time period (i.e., 8 h). Meanwhile, the third index OPCCd of the DNB candidate started to decrease in the second time period and has a local minimum in the same, fifth time period (i.e., 8 h).

Figure 15:
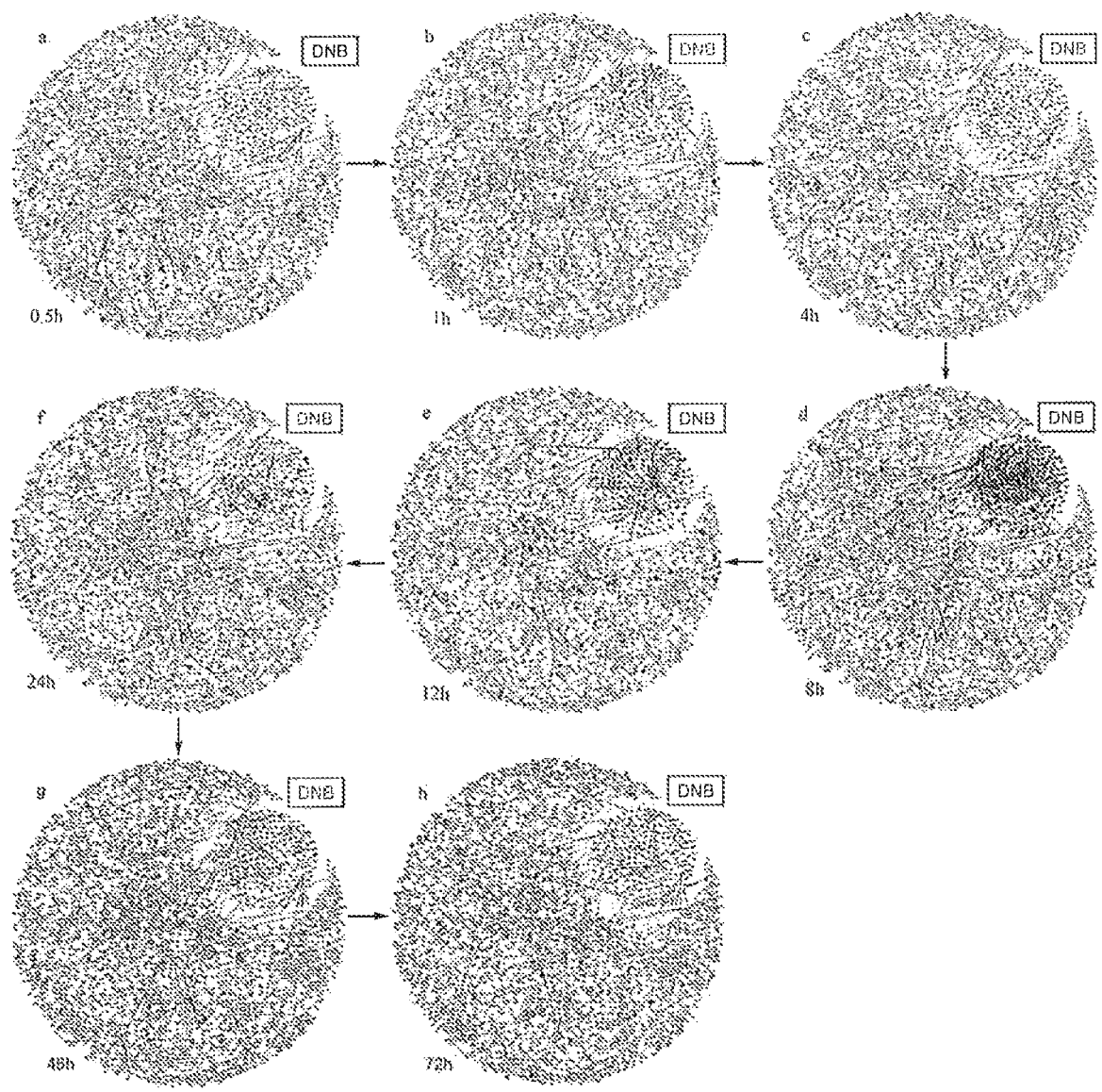
FIG. 15 is chronological maps of exemplary dynamical features of a DNB in a network of case group genes in the first validation example.

The dynamical features of the entire gene network including a DNB are shown in FIG. 15 to intuitively represent the dynamical features of the DNB. FIG. 15 is chronological maps of exemplary dynamical features of a DNB in a network of case group genes in the first validation example. FIG. 15 shows a network of case group genes (3,452 genes and 9,238 links) at sequential sampling points of 0.5, 1, 4, 8, 12, 24, 48, 72 h. The nodes indicated by a "o" are genes of the DNB candidate; those indicated by a "□" are other genes near the nodes of the DNB candidate. The lines linking one node to another represent a correlation of the two nodes. The color concentration of a "o" represents the magnitude of the standard deviation SD of the gene. The color concentration of the line linking the two nodes represents the magnitude of the absolute value of the correlation coefficient PCC of the two nodes. All the maps given as examples in FIG. 15 are drawn using Cytoscape, an open source platform for data analysis.

As illustrated in FIG. 15, the features (SD, PCC) of the DNB candidate change with time, evolving gradually from a normal cluster which behaves in the same manner as the other genes to a DNB. In the fifth period (8 h) shown in e of FIG. 15, the features are the most typical of a DNB, sending off a clear early-warning signal of a pre-disease state (8 h). However, after a transition to a disease state (24 h, 48 h, and 72 h), the DNB member comes to behave the same manner as the other genes.

These results show that the pre-disease state is close to the fifth time period and that the system undergoes a transition to a disease state after the fifth time period.

Therefore, according to the method of DNB-based early diagnosis of a disease in accordance with the present invention, a diagnostic result may be that the fourth time period is giving off such a sign of an early-warning signal for the disease that the disease will deteriorate in the near future. In the fifth time period, a diagnostic result may be that the fifth time period is giving off such a clear disease early-warning signal that there will be a transition to a disease state soon.

Meanwhile, in an actual mouse experiment, the mice in the case group developed lung edema in 8 hours after inhalation of carbonyl chloride. 50% to 60% of them died in 12 hours. 60% to 70% of them died in 24 hours.

Therefore, the diagnostic results from the DNB-based early diagnosis in accordance with the present invention perfectly agree with the actual disease deterioration of the mice.

Second Validation Example

The first validation example validates the effectiveness of the method of DNB-based early diagnosis of a disease in accordance with the present invention by using data from animal experiments. The current validation example further validates accuracy of the diagnosis by the method of DNB-based early diagnosis of a disease in accordance with the present invention by using clinical data from B-cell lymphomagenesis.

FIG. 16 is a table listing diagnosis data for the second validation example. As illustrated in FIG. 16, the samples were divided into five-period groups (rest period (P1), active period (P2), limit period (P3), metastasis period (P4), and invasion period (P5)) based on clinical manifestation, pathological change, and flow cytometry. The numbers of samples for these periods were 5, 3, 6, 5, and 7 respectively. The splenomegaly in the periods was "None," "None," "+/−," "+", and "+++" respectively. The flow cytometry in the periods was "normal rest," "normal active," "abnormal," "mixed," and "B-1 clone" respectively. Control samples were collected in the rest period (P1), and case samples were collected in the other periods (P2 to P5).

Figure 17B:
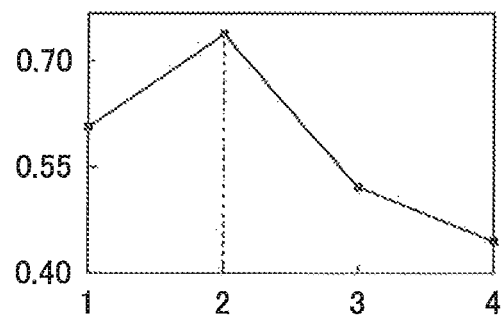
FIG. 17B is a graph representing exemplary time-dependent changes of the average of the absolute values of Pearson's correlation coefficients among cluster members that are detected DNB candidates in the second validation example.
Figure 17C:
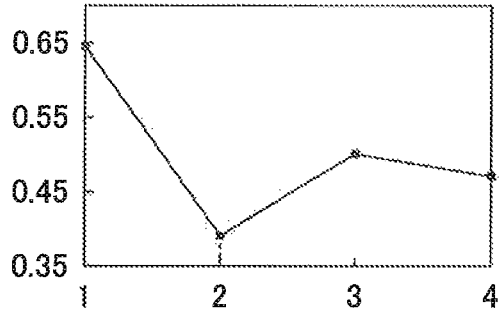
FIG. 17C is a graph representing exemplary time-dependent changes of the average of the absolute values of Pearson's correlation coefficients of cluster members that are detected DNB candidates with other genes in the second validation example.
Figure 17D:
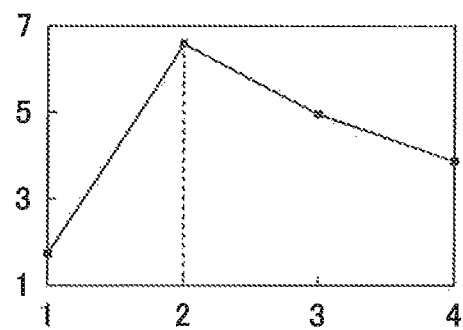
FIG. 17D is a graph representing exemplary time-dependent changes of the average of composite indices for a detected DNB candidate in the second validation example.

A diagnosis was made according to the aforementioned method of DNB-based early diagnosis of a disease from 13,712 genes based on gene expression data obtained from the 26 samples above. Results of the diagnosis are shown in FIGS. 17A to 17D representing indices detected in the genes of the case group for a DNB candidate. FIG. 17A is a graph representing exemplary time-dependent changes of the average SDd of standard deviations of a detected DNB candidate in the second validation example. FIG. 17B is a graph representing exemplary time-dependent changes of the average PCCd of the absolute values of Pearson's correlation coefficients among cluster members that are detected DNB candidates in the second validation example. FIG. 17C is a graph representing exemplary time-dependent changes of the average OPCCd of the absolute values of Pearson's correlation coefficients of cluster members that are detected DNB candidates with other genes in the second validation example. FIG. 17D is a graph representing exemplary time-dependent changes of composite index I for a detected DNB candidate in the second validation example.

In FIGS. 17A to 17D, the horizontal axis indicates numbers for the periods (P1 to P4), and the vertical axis indicates the average SDd of standard deviations (FIG. 17A), the average PCCd of the absolute values of Pearson's correlation coefficients among cluster members (FIG. 17B), the average OPCCd of the absolute values of Pearson's correlation coefficients of cluster members with other genes (FIG. 17C), and the composite index I (FIG. 17D).

As would be clearly understood from FIGS. 17A to 17D, composite index I for the DNB candidate reaches a peak value, sending off the strongest early-warning signal for the disease state, in the second period (P2), or the active period. This diagnostic result perfectly agrees with actual pathological changes. Actual clinical data indicates that the disease starts to deteriorate, the splenomegaly is "+/−," and the flow cytometry is "abnormal" in the limit period that immediately follows the active period. Therefore, the DNB-specific analytic results of the current validation example perfectly agree with the actual clinical data.

In a conventional diagnosis, it is determined that there exists no abnormality because the splenomegaly in the active period is "None" and the flow cytometry in the active period is "normal active," as illustrated in FIG. 16. On the other hand, a diagnosis according to the method of DNB-based early diagnosis of a disease in accordance with the present invention can inform the patient of a result that there is a "sign of abnormality" because an early-warning signal (DNB) indicating a pre-disease state is detected in the active period. The patient can therefore start treatment in an early stage, capable of preventing disease deterioration.

It is validated from the above that the DNB-based early diagnosis of a disease in accordance with the present invention is very effective in the early diagnosis of lymphoma or like complex diseases.

In addition, 22 genes and TFs are among the DNBs detected in the current validation example. 13 genes of them are clearly related to B-cell lymphomagenesis. Furthermore, 8 of the 13 genes are identified to be master regulators for proliferation. Therefore, the DNB in accordance with the present invention should be very useful for treatments and drug manufacturing for complex diseases because it not only gives a sign of abnormality to the patient in an early stage in the form of an early-warning signal indicating a pre-disease state, but also specifically identifies genes related to the disease.

The embodiments are a disclosure of only a few of countless examples of the present invention and may be altered if necessary in view of the nature of the disease, detection targets, and various other conditions. Especially, the factors may be any measurement data provided that the information is obtained in measurement on a biological object. The measurement data may be, for example, the aforementioned gene-, protein-, or metabolite-related measurement data or may be obtained by quantifying various conditions of an organ based on an image output of the interior of the body from a measuring instrument, such as a CT scanner. Furthermore, the measurement data may come from a non-image source, for example, measured and quantified voice or sound that comes from the interior of the body.

REFERENCE SIGNS LIST

1 Detection device
10 Control unit
11 Storage unit
12 Memory unit
13 Input unit
14 Output unit
15 Acquisition unit
11a Detection program

The invention claimed is:

1. An early diagnosis method of complex diseases for which no reliable disease models are developed, the method comprising the following steps:
    collecting samples of a biological object to be measured at a plurality of time points;
    acquiring, by an acquisition unit, high-throughput data on a plurality of factors of the samples of the biological object to be measured;
    classifying the factors into clusters based on a correlation of time-dependent changes of the high-throughput data for each factor;
    calculating each cluster's maximum composite index value, wherein the composite index value is a product of:
    (i) a first index that is an average of the absolute values of Pearson's correlation coefficients of the high-throughput data for each factor in the cluster,
    (ii) a second index that is an average of the absolute values of Pearson's correlation function of the high-throughput data for the factors inside the cluster with the high-throughput data for the factors outside the cluster, and
    (iii) a reciprocal of a third index that is an average standard deviations of the high-throughput data for each factor in the cluster;
    performing significance analysis on the cluster that has the maximum composite index and adopting the composite index of the cluster, which is referred to Dynamic Network Biomarker (DNB), as an early-warning signal of a pre-disease state if the cluster is detected to be significant; and
    sending off the strongest warning signal to a physician at a peak time point when the composite index turns from increase to decrease so that the physician makes a distinction between a pre-disease state and a normal state, wherein the distinction having been difficult by a conventional diagnosis method.

2. The method as set forth in claim 1, further comprising a difference verification step of verifying whether or not the high-throughput data for each of the factors has significantly changed with time,
wherein the factors in the performing significance analysis step are the factors whose significance in the time-dependent changes is verified by the difference verification step.

3. The method as set forth in claim 2, wherein, in the difference verification step, it is verified, based on a comparison of the high-throughput data for each of the factors and reference data that is predetermined, whether or not the factors have significantly changed with time.

4. The method as set forth in claim 1, wherein the factors include at least one of a gene-related measured item, a protein-related measured item, a metabolite-related measured item, and a measured item related to an image obtained from the biological object.

5. The method as set forth in claim 1, further comprising a step of outputting, based on the emergence of the DNB detected by the performing significance analysis step, information that assists in determining at least one of the following: whether there exists an abnormality in the biological object; validity of determination of the pre-disease state that precedes the transition from the normal state to the disease state of the biological object; and a disease whose symptoms could possibly be developed by the biological object.

6. A non-transitory computer readable medium storing a program causing a computer to execute an early diagnosis of complex diseases for which no reliable disease models are developed,
wherein the program causes the computer to execute the following steps:
collecting samples of a biological object to be measured at a plurality of time points;
acquiring high-throughput data on the a plurality of factors of the biological object to be measured;
classifying the factors into clusters based on a correlation of time-dependent changes of the high-throughput data for each factor;
calculating each cluster's maximum composite index value, wherein the composite index value is a product of:
(i) a first index that is an average of the absolute values of Pearson's correlation coefficients of the high-throughput data for each factor in the cluster,
(ii) a second index that is an average of the absolute values of Pearson's correlation function of the high-throughput data for the factors inside the cluster with the high-throughput data for the factors outside the cluster, and
(iii) a reciprocal of a third index that is an average standard deviations of the high-throughput data for each factors in the cluster;
performing significance analysis on the cluster that has the maximum composite index and adopting the composite index of the cluster, which is referred to Dynamic Network Biomarker (DNB), as an early-warning signal of a pre-disease state if the cluster is detected to be significant; and
outputting on an output unit the early-warning signal of a pre-disease state in a graphic form so as to intuitively show a disease risk.

7. The non-transitory computer readable medium storing the program as set forth in claim 6,
wherein the program causes a computer to execute a difference verification step of verifying whether or not the high-throughput data for each of the factors has significantly changed with time, and
wherein the factors in the performing significance analysis step are the factors whose significance in the time-dependent changes is verified by the difference verification step.

8. The non-transitory computer readable medium storing the program as set forth in claim 7, wherein the program causes a computer to verify, as the difference verification step, whether or not the factors have significantly changed with time based on a comparison of the high-throughput data for each of the factors and reference data that is predetermined.

9. A device for an early diagnosis of complex diseases for which no reliable disease models are developed, comprising:
collecting unit configured to collect samples of a biological object to be measured at a plurality of time points;
an acquisition unit configured to acquire high-throughput data on a plurality of factors of the biological object to be measured;
a classification unit configured to classify the factors into clusters based on a correlation of time-dependent changes of the high-throughput data for each factor;
a calculation unit configured to calculate each cluster's maximum composite index value, wherein the composite index value is a product of:
(i) a first index that is an average of the absolute values of Pearson's correlation coefficients of the high-throughput data for each factor in the cluster,
(ii) a second index that is an average of the absolute values of Pearson's correlation function of the high-throughput data for the factors inside the cluster with the high-throughput data for the factors outside the cluster, and
(iii) a reciprocal of a third index that is an average standard deviations of the high-throughput data for each factors in the cluster;
a significant analysis unit to perform significance analysis on the cluster that has the maximum composite index and adopting the composite index of the cluster, which is referred to Dynamic Network Biomarker (DNB), as an early-warning signal of a pre-disease state if the cluster is detected to be significant; and
an output unit configured to output the early-warning signal of a pre-disease state in a graphic form so as to intuitively show a disease risk.

* * * * *